United States Patent [19]

Cais et al.

[11] Patent Number: 4,832,850

[45] Date of Patent: May 23, 1989

[54] METHOD AND DEVICE FOR MASS TRANSPORT AND SEPARATION THROUGH SELECTIVE BARRIERS

[75] Inventors: Michael Cais; Moshe Shimoni, both of Haifa, Israel

[73] Assignee: Technion Research and Development Foundation, Ltd., Haifa, Israel; a part interest

[21] Appl. No.: 821,768

[22] Filed: Dec. 27, 1985

Related U.S. Application Data

[63] Continuation-in-part of Ser. No. 542,906, Oct. 20, 1983, abandoned, which is a continuation of Ser. No. 270,411, Jun. 4, 1981, abandoned.

[30] Foreign Application Priority Data

Jul. 21, 1980 [IL] Israel ........................................ 60645

[51] Int. Cl.$^4$ ............................................. B01D 15/04
[52] U.S. Cl. ..................... 210/638; 210/650; 210/652; 210/682; 210/662; 210/780; 210/786; 436/178; 422/101
[58] Field of Search ............... 210/780, 786, 650, 638, 210/652, 682, 662; 436/178; 422/101

[56] References Cited

U.S. PATENT DOCUMENTS

| | | | |
|---|---|---|---|
| 2,524,362 | 10/1950 | Smith | 210/359 X |
| 3,027,799 | 4/1962 | Weichselbaum | 422/104 X |
| 3,464,798 | 9/1969 | Kilthau | 210/359 X |
| 3,512,940 | 5/1970 | Shapiro | 210/359 X |
| 3,512,948 | 5/1970 | Glaser et al. | 65/10.1 |
| 3,802,843 | 4/1974 | Kim | 422/101 |
| 3,969,250 | 7/1976 | Farr | 210/927 X |
| 4,021,352 | 5/1977 | Sarstedt | 210/359 |
| 4,035,150 | 7/1977 | Jaffe | 436/178 X |
| 4,205,952 | 6/1980 | Cais | 424/12 X |
| 4,210,623 | 7/1980 | Breno et al. | 422/101 |
| 4,454,231 | 6/1984 | Cais et al. | 436/500 |

FOREIGN PATENT DOCUMENTS

1140463 2/1983 Canada .
1508844 4/1978 United Kingdom ................ 210/359

Primary Examiner—Ernest G. Therkorn
Assistant Examiner—Coreen Y. Lee
Attorney, Agent, or Firm—Foley & Lardner, Schwartz, Jeffery, Schwaab, Mack, Blumenthal & Evans

[57] ABSTRACT

The present invention relates to a new technique and device for mass transport operation and physical separation, being substantially quantitative and involving selective barriers. According to the new technique, the mass transport through the selective barrier and physical separation are carried out in the same device. The device consists of a mixing-reservoir into which is fitted snugly a mixer-separator, having a channel in the vertical axis of the mixer-separator, the mixer-separator being provided with means for accumulating a gas pocket to decrease the pressure exerted on the barrier. The completely solid-free liquid passing through the selective barrier is removed by pushing in the mixer-separator, said liquid being accumulated in a collecting container. Typical examples of such selective barriers are: membrane, bed of adsorbent material, paper, plastic, glass and metal filters or any other porous material, hollow fibers etc. The new technique and device can be successfully utilized in any operation involving separation of solids from liquids and particularly useful in immunoassay, sterilization, ultra-filtration, desalination by reverse osmosis, etc.

15 Claims, 7 Drawing Sheets

FIG. 4b
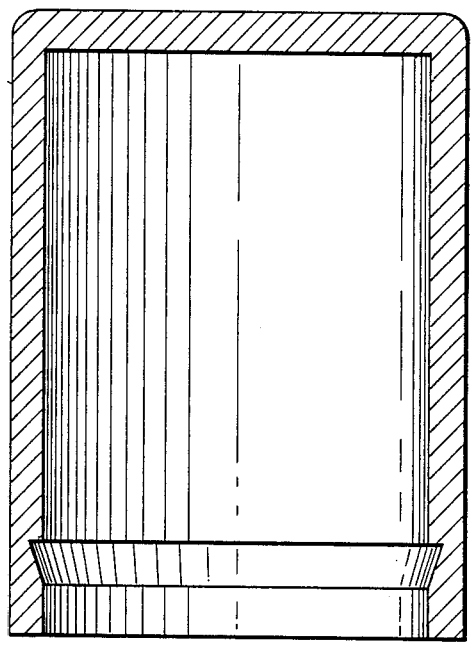
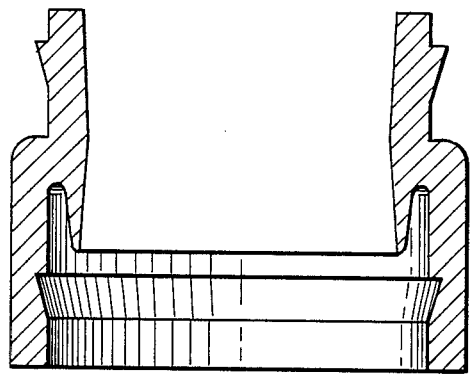
FIG. 4a

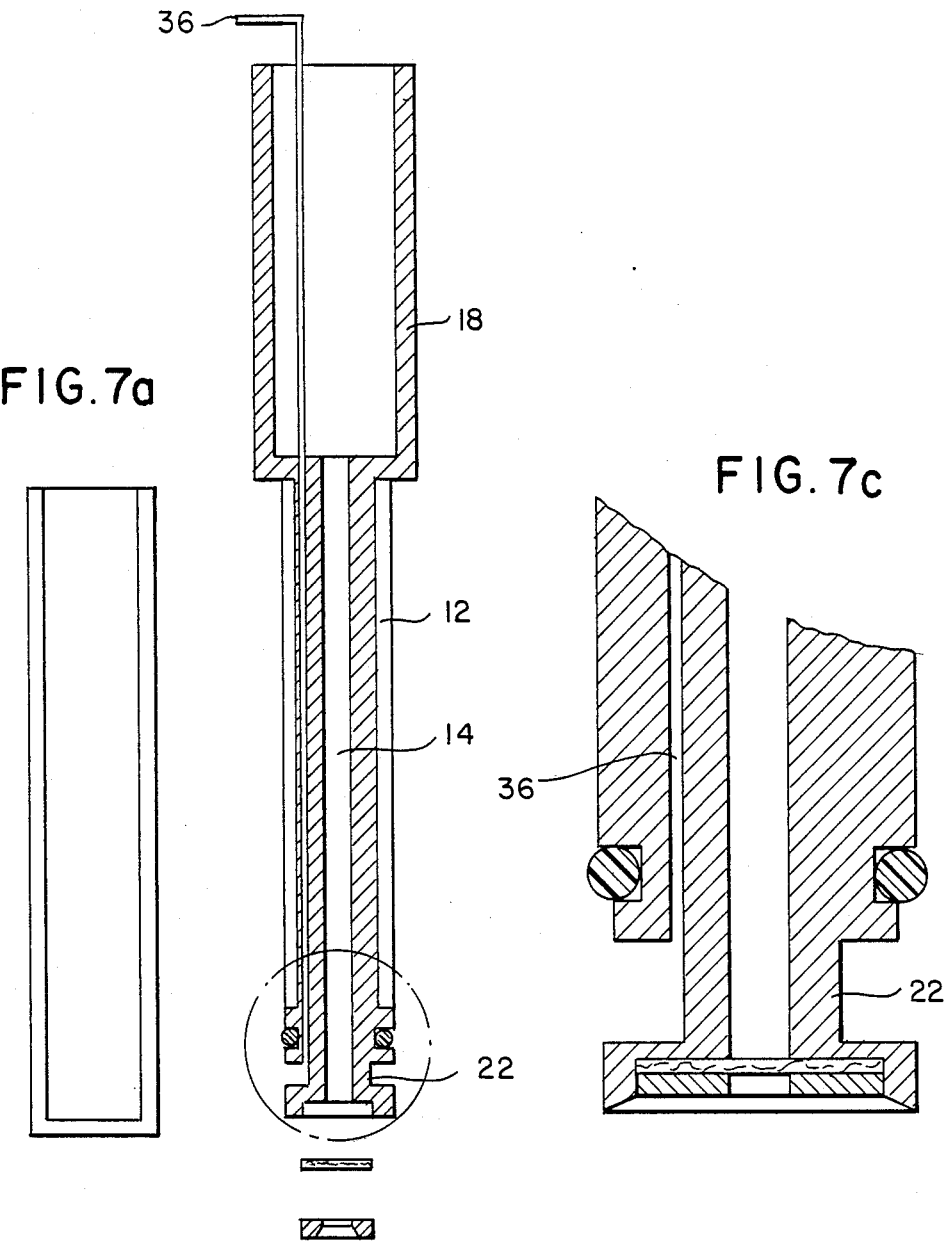

METHOD AND DEVICE FOR MASS TRANSPORT AND SEPARATION THROUGH SELECTIVE BARRIERS

This application is a continuation in part of the application Ser. No. 542,906 filed on Oct. 20, 1983, which was a continuation application Ser. No. 270,411 filed on June 4, 1981, both now abandoned.

BACKGROUND OF THE INVENTION

The present invention relates to improvements in the technique for mass transport operation and physical separation involving barriers. More particularly the invention relates to improvements in the technique for carrying out the transport of one or more components from a liquid or solid phase to another liquid or solid phase.

In our previous U.S. Pat. No. 4,454,231 a method and device have been disclosed for carrying out mass transfer operation and phases separation in the same piece of equipment, the device being referred to as "LIDEX" (Liquid Extraction Separation Device). The method comprises the introduction of the two liquids to be contacted into the mixing-reservoir, mixing the liquids and thus performing the mass transfer of the desired components from one phase to another. After allowing the formation of the interphase between said two liquids, the mixer-separator is pushed in until it reaches the interface, the liquid upper phase being forced through the bore of a sealing element located at the bottom of the mixer-separator and through a channel which traverses the vertical axis of the mixer-separator being accumulated into a container above the mixer-separator element. The method was found to be most efficient for a number of uses involving mass transfer and phase separation with liquids only and particularly for the immunoassay technique being extremely wide, versatile and competing very favourably with other known methods.

The method described in said previous patent was invented as a result of the efforts invested in order to find an efficient method to be applied in conjunction with our basic patent application on the use of liquid-liquid extraction technique for specific binding assay (Canadian Pat. No. 1,140,463). The method was found to be most suitable for any immunoassay technique such as radioimmunoassay, enzyme immunoassay, free radical assay or metalloimmunoassay (as described in U.S. Pat. No. 4,205,952). The use of the novel device according to the previous U.S. Pat. No. 4,454,231 provided a very simple and efficient method for the extraction procedure and following the separation of the liquid phase in the upper container of the device, it was possible to determine directly in the liquid phase by appropriate analytical methods any minute concentration of chemical substances.

One basic characteristic of the method and device disclosed in the previous U.S. Pat. No. 4,454,231, is the existence of a continuous region in the form of a channel, free of any obstruction, connecting the orifice bore at the base of the sealing element, with the container located at the upper end of the mixer-separator. Thus when the mixer-separator is pushed into the mixing reservoir, the forced liquid will flow up smoothly, without encountering any hindrance.

Today there is a large number of examples showing the successful applicability of the method described in our previous patent application in various fields involving mass transfer and physical separation between two liquid phases. The phase "mass transfer" refers to the motion of molecules or fluid elements caused by some form of potential or driving force and it includes molecular diffusion, transport by convection and simple mixing. Mass transfer is involved wherever a chemical reaction takes place. The reacting substances must come together if the reaction is to proceed. In the case of a reversible reaction, the concentration of reactants and products at any instant can be controlled if one or more reaction components are removed by mass transfer to a second phase in which no reaction takes place. Of particular importance to the problem in hand is transfer between two phases across an interface since this phenomenon is involved in most separation processes. Any method of contacting two phases which results in the selective interphase transport of one of the constituents can form the basis of a separation process. The selectivity can be the result of different equilibrium relations for the different species or it may be due to different rates of transport of the several constituents. Of particular interest for the present invention is the problem of mass transfer between a fluid and suspended particles and more particularly mass transport through selective barriers to achieve separation between the fluid and suspended particles, once the mass transfer effect has produced the desired degree of the physico-chemical and-/or immunological reactions.

The prior art also describes a number of separation methods in immunoassay procedures for the bound and free fractions based on solid phase adsorption, various solids being suggested as adsorbants (e.g., charcoal, resin, silica, florisil etc.) of free antigens or precipitation agents for the bound phase, all of which end up with a system of suspended particles in a liquid medium. The selection of any particular technique is determined by consideration of many interrelated factors such as solubility of compound, characteristics of antiserum, fraction to be counted, degree of non-specific binding, and type of radioisotope. However one feature which is common to all the above methods is the need for a centrifugation step to effect aggregation of the suspended solid particles followed by a decantation or suction step, to physically separate the solid and liquid phases. Another main disadvantage of these methods is the fact that no full separation can be obtained between the bound antigen-antibody complex and the free unbound antigen. A recent elegant method in the solid phase adsorption of antibody is adsorption of antibodies to plastic tubes. Accordingly, a number of coated tubes are prepared in advance. The preparation and storage of large numbers of such tubes is a serious drawback in addition to the fact that these tubes are sensitive to variations in serum protein content.

To the best of our knowledge there is no prior art on the method of mass transfer and physical separation of the phases, both operations being carried out in the same device in accordance with the present invention.

In principle, the device according to the previous patent application could be conceived to be also useful concerning mass transport operation, from one phase to another, even when two different phases e.g. liquid-solid are utilized. However in this case some difficulties would be expected in the physical separation of the phases, since the liquid phase aspirated through the channel will also induce the entrainment of some solid phase particles.

Based on the principle of an ampoule having a hollow piston as disclosed in the U.S. Pat. No. 2,524,362, a test tube filter device having a hollow plunger with a porous bottom portion as filter, is described in the U.S. Pat. No. 3,512,940. A specific application using the principle of said device, has been later on described for separation of blood fractions in a number of U.S. Patents and German patent applications. A typical illustration of one of these publications are the German patent application Nos. 2,415,618 and 2,454,918 (or their corresponding U.S. Pat. No. 4,021,352 and U.K. Pat. No. 1,508,844).

The device described in these patents is specifically related to an apparatus for separating blood fractions. A piston with a hollow riser tube has at its bottom end a filter section which is permeable for the top layer fraction only. The piston is inserted into the cylindrical vessel and pushed downwardly, but only to the point where it is slightly above the interface of the heavier fraction. Special care has to be used in operating this device to avoid mixing of the two phases during the downward movement of the piston into the cylindrical vessel. The device has at its top a stopper which can be either open or closed.

Another device, to be used for blood separation, is described in the U.S. Pat. No. 3,969,250. According to the device disclosed therein, a plunger is movable into an outer tubular member closed at the lower end. A piston head having a downwardly extending inlet tube is attached to the lower end of the plunger. On the inlet tube is mounted an elastic membrane and below this barrier is positioned a slidingly removable piston rubber seal. During use, the rubber piston seal is separated from the surface of the serum, by an air column in order to avoid falling down of any blood cell, debris or solids wiped from the inner wall of the blood tube by the rubber piston seal, as the piston is forced downwardly.

The above devices are specifically for a qualitative determination, to be useful for processing blood serum specimens and separating the fractions thereof.

In principle, the device according to our previous U.S. Pat. No. 4,454,231 could be conceived to be also useful concerning mass transport operation from one phase to another, even when two different phases e.g. liquid-solid are utilized. However in this case some difficulties would be encountered in the physical separation of the phases, since the liquid phase aspirated through the channel will also induce the entrainment of some solid phase particles.

SUMMARY OF THE INVENTION

It is an object of the present invention to provide an improved method for carrying out mass transport operation of one or more components from one phase to another phase, the phases being both liquids, or liquid and solid, or liquid-gas and solid, involving a physical separation of said phases on a substantially quantitative basis. It is another object of the present invention to provide a novel device for the separation of two or more phases on a substantially quantitative basis. It is yet another object of the present invention to provide an improved method and simple device which is capable of extremely wide versatility and applications to both laboratory and industrial operations,. Thus, the invention consists in an improved method and device for carrying out mass transport operations of one or more components from one phase to another phase, the phases being both liquid, or liquid-solid or liquid-gas-solid, or liquid-gas-liquid, said mass transport and physical separations being carried out in the same device, which comprises the introduction of the phases to be contacted into a vertical mixing reservoir, mixing the components, pushing in a mixer-separator possessing at least one barrier and a sealing element located above said barrier the clear liquid phase being aspirated through a barrier and the bore of the sealing element, being conveyed through at least one channel into the collecting container, wherein said mixer-separator is provided with means for accumulating of gas pocket to decrease the pressure exerted on the barrier.

One of the main features which enables the broad applicability of the improved method according to the present system and differs from that described in the previous patent application, is the special design of the mixer-separator. Whereas in the previous patent application, there is a continuous empty zone from the base of the mixer-separator passing through the orifice bore and the channel to the upper collecting container, according to the present invention the intercalation of a barrier causes the partition of said continuous zone into two separated zones, one above the barrier and the other below the barrier. The intercalation of the barrier into the mixer-separator gives rise to a certain resistance to the flow of the liquid phase through the barrier into the mixer-separator. As a result of this resistance and unless the downward movement of the mixer-separator is impractically slow, some of the liquid will penetrate by flowing around the sealing element located at the base of the mixer-separator and will rise up along the walls of the reservoir during the downward gliding of the mixer-separator. This would of course interfere with the entire separation method, and consequently with the accuracy of the quantitative determination of the separated fractions. It was found in accordance with the method of the present invention that the existence of a critical amount of air, present between the barrier location and the sealing element, and sufficient enough to decrease the pressure induced by the incorporation of a barrier, would eliminate said liquid penetration alongside the walls of the mixing-reservoir, the physical separation of the phases being complete and most accurate.

The term barrier as used in the present specification, means any fixed or mobile bed in a loose or compact form, having the property of selectively separating the undesired solid, liquid or gaseous component(s) from the mixed phases present in the mixing-reservoir. Examples of such barrier are: membrane, bed of adsorbent material, filter cloth, filter paper, sintered glass, metal filter, disc of compact ceramic, porous material, hollow fibers etc. Further in the context of the specification it should be understood that the illustration of one type of barrier is likewise applied to any other example of barrier according to the specific case.

Today membrane processes are utilized in industry, biomedical engineering and other fields and a large number of publications are encountered. In its broadest definition a membrane means a region of discontinuity interposed between two phases. Membranes vary in their make-up from the relatively crude structure of a screen to extremely fine configurations of only one molecular layer thick. The role of a membrane in a separation process is to act a selective barrier. It should permit preferred passage of a certain component out of the mixture. Macroscopic processes, like filtration, do not rely on the molecular properties of a membrane. However, microscopic processes, which constitute the majority of the membrane processes, are mostly due to molecular interaction between membrane and fluids.

The process of separation through a membrane involves several fundamental physical phenomena, as the constituents in the feed stream pass over the membrane, into it, through it, and finally leave the membrane on the other side. The basic unit operations involved in said separation are permeation and diffusion. Whereas the term diffusion is usually referring to a molecular process the term permeation stands for a more general phenomenon of mass transmission encompassing a variety of transport mechanisms. Among the factors affecting such mechanisms the following could be mentioned: the concentration gradient, pressure gradient, electric potential gradient or the temperature gradient. Depending on the specific permeation mechanisms, the flow process will be called diffusion, osmosis, electrodialysis, electro-osmosis dialysis, reverse osmosis, ultrafiltration, electrophoresis and so forth.

For the present invention it seems that the most adequate classification of membranes would be that based on their action, all of them being suitable as a barrier for use with the mixer-separator described in the present invention. This classification considers the following main groups:

a. Adsorptive membranes such as microporous membranes (inorganic and organic): porous Vycor*, activated charcoal, silica gel and the like in the form of compressed powders, and reactive membranes such as a chemically reactive material contained in the membrane and which reacts with one of the permeating constituents.

*Trademark b. Diffusive membranes such as: polymeric membranes possessing diffusive solubility, flow metallic membranes and glass membranes with molecular state or affinity phenomena.

c. Ion exchange membranes such as: cation-exchange resins and anion-exchange resins.

d. Osmotic and ultrafiltration membranes such as: regular osmotic, electro-osmotic membrane and reverse osmosis membrane.

e. Non-selective membranes having an inert behaviour such as: fritted glass and filters or screens.

The selection of a membrane from the above broad classes will be according to the specific use of the device described in the present invention. Thus for instance in case of water desalination, one would select the known anisotropic cellulose acetate or an equivalent membrane which possesses the specific requirement of reverse-osmosis process. Other synthetic resins such as polyamides have now also been suggested as suitable membranes for this purpose. As known in reverse osmosis there is a preferential permeation of the solvent through the membrane with the exertion of an external pressure, said pressure being larger than the difference of the osmotic pressure across the membrane.

It is generally considered that the microporous inorganic membranes are of great interest and potential value for many industrial and biomedical uses. This is because there are many membranes that permit virtually complete separation of certain constituents in a single-stage operation.

Today there are available a wide variety of chemically and thermally stable engineering thermoplasts and fiber-forming polymers such as polyvinyl chloride, polyacrylonitrile, poly-carbonate, polysulfone and aliphatic and aromatic polyamides. By controlled solvent-casting and non-solvent precipitation techniques, these can be converted into a broad spectrum of assymmetric, ultramicroporous membranes with the desired properties. As a consequence it became possible to produce high-flux membranes which can retain molecules as small as 500 daltons and others that can pass macromolecules as large as 300,000 daltons.

Summing up, a membrane for the present invention would be selected from any adequate material, which is impervious to one of the phases, or to one constituent or more from one of said phases, in the direction of the mixer-separator movement. In its simplest form, in a solid-liquid separation it will be a porous disc, made of an inert material chosen so that the pores are smaller than the solid particles present in the system to be separated.

It is beyond the scope of the present specification to enter into further details and theoretical aspects of membranes and the mechanisms involved; a person skilled in the art will certainly select the proper membrane for the specific use envisaged, it being understood that any type of membrane could be utilized in the method according to the present invention.

The large number of existing membranes is of assistance to the versatility of utilizing the method, according to the present invention and the device described herein. As an example of a particular use for the method and device, it should perhaps be mentioned the sterilization of water using a suitable membrane for obtaining bacteria-free potable water. One could even envisage that any travelling person, could carry with him for personal use such a device, getting potable water from any source of brackish water or contaminated water.

Based on the same approach to obtain a discontinuity in the channel of the mixer-separator, it is possible to intercalate therein more than one barrier. Such a device would be accordingly most useful for chromatographic bed adsorbents, the exertion of the slight pressure by the mixer-separator being advantageous for the operation. As known the principle behind the chromatographic technique, lies in the repeated subjection of a mixture of chemical compounds to extraction by a liquid or adsorption on a solid surface. The mixture is moved physically on a stationary phase which may be either a solid or a liquid immobilized in the pores of a solid. The various components of the mixture migrate from the moving phase into the stationary phase and back again into the moving phase. If differences in solubility or adsorption exist between the components of the mixture, the more strongly adsorbed or more soluble compounds will gradually lag behind the less strongly adsorbed or less soluble ones. The moving phase may be a mixture of gases, a mixture of liquids, or a liquid containing dissolved solids. The two basic different physical separating principles involved in chromatography, i.e. separation due to difference in solubility in the immiscible phases—so called partition chromatography—and separation due to differences in adsorption on a solid surface—so called ion exchange chromatography—can be also successfully utilized by the new device and method according to the present invention.

One of the main features which enables the successful use of mass transport and separation through a selective barrier according to the present invention, is the provision of means on the mixer-separator, for accumulating an air pocket to decrease the pressure exerted on the membrane. During operation of the mixer-separator a determined amount of air is entrapped in the air pocket, which upon compression acts as a cushion or shock absorber to take up part of the pressure resulting from the membrane resistance to the liquid flow. Upon decompression, the entrapped amount of air will force back into the mixing-reservoir A any liquid which may have creeped up in the space between the inner walls of the mixing-reservoir A and the outer walls of the terminal end of the mixer-separator. The amount of air entrapped by said means on the mixer-separator will depend on many factors such as the type of barrier, constituents of the mixtures to be separated and the particular conditions exerting in the separation system. A theoretical approach to calculate the pressure of said determined amount of air is hereafter illustrated.

Let us consider the following physical model based on the mixer-reservoir and the mixer-separator with a sealing element, an air pocket and a membrane barrier. In the initial position of the mixer-separator, let $P_1$ be the atmospheric pressure from above the mixer-separator, $V_1$ the volume in the mixer-reservoir below the membrane cavity and $V_b$ the volume in the air pocket between the sealing element and the lower end of the mixer-separator where the membrane is located. During the downward movement of the mixer-separator, $P_2$ is the pressure from above the mixer-separator, $V_2$ the volume in the mixer-reservoir, $V_b$ the volume in the air pocket, and $P_M$ the upward pressure at the membrane surface. We shall make the simple physical assumptions of ideal gas and incompressible liquid behaviour. The applied pressure is $\Delta P = P_2 - P_1$. If we neglect the energy loss resulting from liquid-vessel walls friction one can write equation (i) as follows: $W_p = W_2 + W_b + W_m$ where $W_p$, $W_2$, $W_b$ and $W_m$ are respectively the work of the mixer-separator piston, the work needed to pump up the liquid, the work needed to compress the gas in the air pocket and the work required to transfer the liquid through the membrane. The mechanical work of the mixer-separator is simply given by equation (ii): $W_p = -P_2(V_2 - V_1)$. The work required to pump up the liquid is equation (iii): $W_2 = -P_m(V_2 - V_1)$. The isothermal work to compress the gas in the air pocket, equation (iv) is:

$$W_b = - \int_{P_1}^{P_m} P dv = -P_1 V_b \ln P_1/P_M.$$

The work required to transfer the liquid through the membrane is proportional to the difference between the applied pressure $\Delta P$ and the osmotic pressure $\pi$, and is given by equation (v): $W_M = k(\Delta P - \pi)$ where k is a membrane constant. By substituting equations (ii)-(v) in equation (i) one obtains equation (vi): $P_2 = \alpha P_M + \beta \ln P_M - \gamma$, where $P_m > 1$ and $\alpha, \beta$ and $\gamma$ are positive parameters:

$$\alpha = 1 + \frac{k}{V_1 - V_2}; \beta = + \frac{P_1 V_b}{V_1 - V_2};$$

$\gamma = [P_1 V_b \ln P_1 + k(P_1 + \pi)]/V_1 - V_2$.

From equation (vi) one can see that for a given pressure $P_2$ the positive logarithmic term which results from the presence of the air pocket on the mixer-separator reduces the pressure at the membrane surface $P_M$ (for $P_M > 1$ atm.) Let us demonstrate the above result for a special example where $P_1 = 1$ atm in two cases: Case I where the mixer-separator possesses means for an air pocket; Case II where the mixer-separator does not possess means for an air pocket; in Case I, $P_2 = \alpha P_M{}^I + \beta \ln P_M{}^I - \gamma$. In Case II, $P_2 = \alpha P_M{}^{II} - \gamma$. Therefore: $P_M{}^{II} - P_M{}^I = B/\alpha - \ln P_M{}^I > 0$. In other words pressure at the membrane $P^{II}$ (without air pocket) will be greater than $P_M{}^I$ (with air pocket). Laboratory experimental results have shown that even for very small air pockets $P_M{}^{II}$ can be greater than $P_M{}^I$ by 25% or more.

Means on the mixer-separator for accumulating an air or other gas pocket can be of several types. One approach is to insert grooves on the mixer-separator, the air being accumulated in the grooves. The grooves can be of any particular shape or their direction being horizontal, vertical or even spiral. Another approach is to provide the air pocket in the form of an air exit tube (or tubes) which connects the space present between the sealing element and upper liquid surface with an air (or other gas) container, separate from the mixer-separator system. An illustration of this embodiment is given in FIG. 7. The improved device and method according to the present invention is technically very simple, expeditious and inexpensive and should be considered as an ideal method in liquid-liquid extraction, liquid-solid extraction, liquid-gas-solid extraction or liquid-gas-liquid extraction. The last two systems could be operated based on a different solubility of gas in a solid and/or liquid substance.

BRIEF DESCRIPTION OF THE DRAWINGS

In the drawings:

FIGS. 4A-B demonstrates one type of top or stopper for the separator;

FIGS. 7A-C illustrates yet another form of mixer-separator.

DETAILED DESCRIPTION OF THE PREFERRED EMBODIMENTS

Figures 1A, 1B, 1C, 1D, 1E, 1F, 1G:
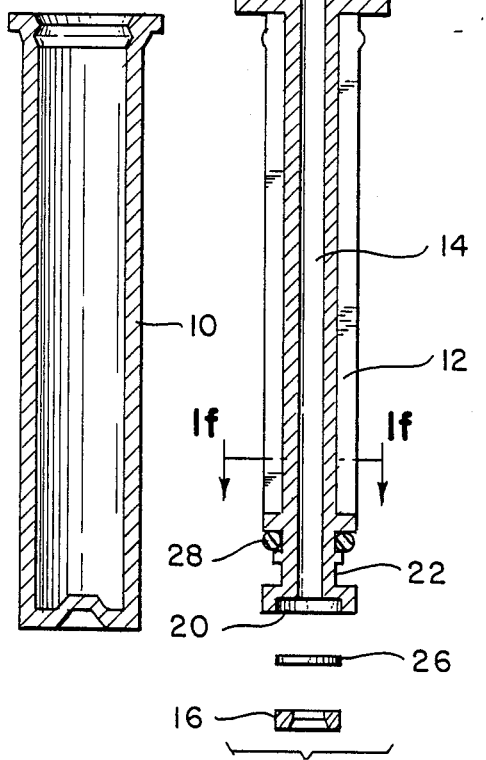
FIGS. 1A-G illustrates the new separator system for the present invention with the individual components making up the system shown as FIGS. 1a-g.

The new separator system is illustrated schematically in FIG. 1. For brevity and convenience we shall refer to this device as Lidex PS (Precipitate Separator) to distinguish it from the mixer-separator described in the previous patent application and which will be referred to herein as LIDEX LS (Liquid Separator). The LIDEX PS system (FIG. 1) consists of the following main components: a specially designed mixing-reservoir 10 (FIG. 1a); a mixer-separator 12 (FIG. 1b) which at its upper end is shaped in the form of a collecting container 18 and at its lower end has a cavity 20 in which can be fitted a suitable membrane 26 as barrier, the latter being held tightly in place by a ring disc 16; a sealing element 28 (rubber O-ring) at a preselected distance from the lower end of the separator-mixer 12 which allows the latter to fit snugly into a slide along the inner wall of the mixing-reservoir 10; a groove 22 between the membrane cavity and the O-ring (vide infra); a channel 14 which traverses axially the mixer-separator 12, connecting the membrane cavity 20 with the collecting container 18; a stopper 34 (FIG. 1c). On operation the mixer-separator 12 is pushed down in the mixing-reservoir 10. This causes the liquid phase to be aspirated through the orifice bore of the ring disc 16, then through channel 14 to finally be accumulated into the collecting container 18. The membrane 26 in the cavity 20 will act as a selective barrier, preventing the suspended solid particles from being transported together with the liquid phase into the container 18.

Figure 3:
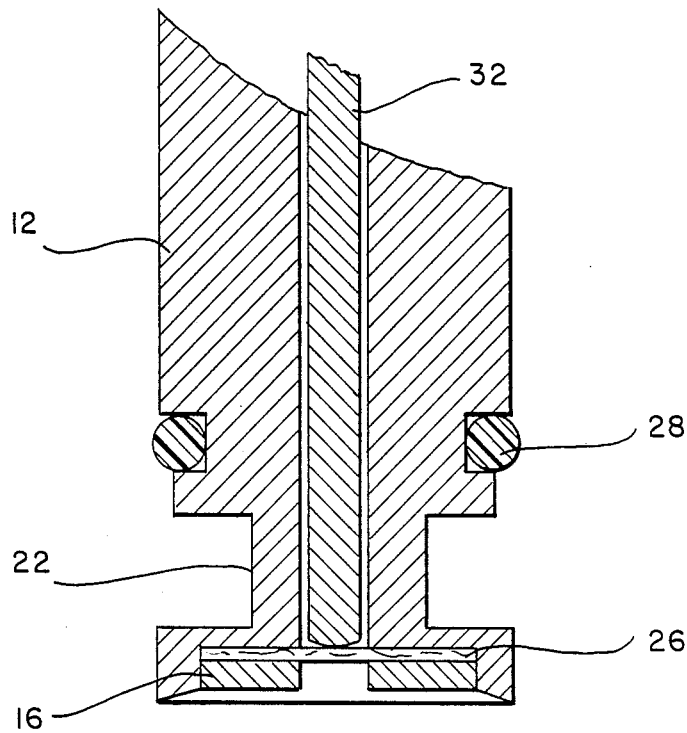
FIG. 3 shows an enlargement of a portion of the separator of FIG. 2.

The groove 22, (FIGS. 1b and 3) between the membrane cavity 20 and the O-ring 28, plays a highly crucial role. During operation of the separator 12 the groove 22 serves to entrap a determined amount of air which upon compression acts as a cushion to take up part of the pressure resulting from the membrane resistance to the liquid flow and upon decompression it forces back into the tube any liquid which may have crept up in the space between the inner walls of the mixing-reservoir 10 and the outer walls of the terminal end of the mixer-separator 12. The gas cushion is maintained during the entire movement of the mixer-separator into the mixing reservoir until all the liquid phase is forced through the barrier. Two additional distinct features of the mixer-separator are the protrusions at the top of, and just below the collecting container 18 (FIGS. 1b and 1e). Upon completion of the sliding movement of separator 12 in the separation operation (vide infra), these protrusions snap on tightly into the respectively located grooves in the stopper 34 and the inner rim of the mixing-reservoir 10, thus effectuating a hermetical closure of the entire device. No accidental spilling of the contents of the tube can occur, thus providing a high degree of safety from radiation hazards in handling radioactive reagents in the course of the RIA assay protocol, as opposed to the dangers inherent in the ubiquitous decantation of supernatants following centrifugation in currently used RIA procedures.

Figures 2A, 2B:
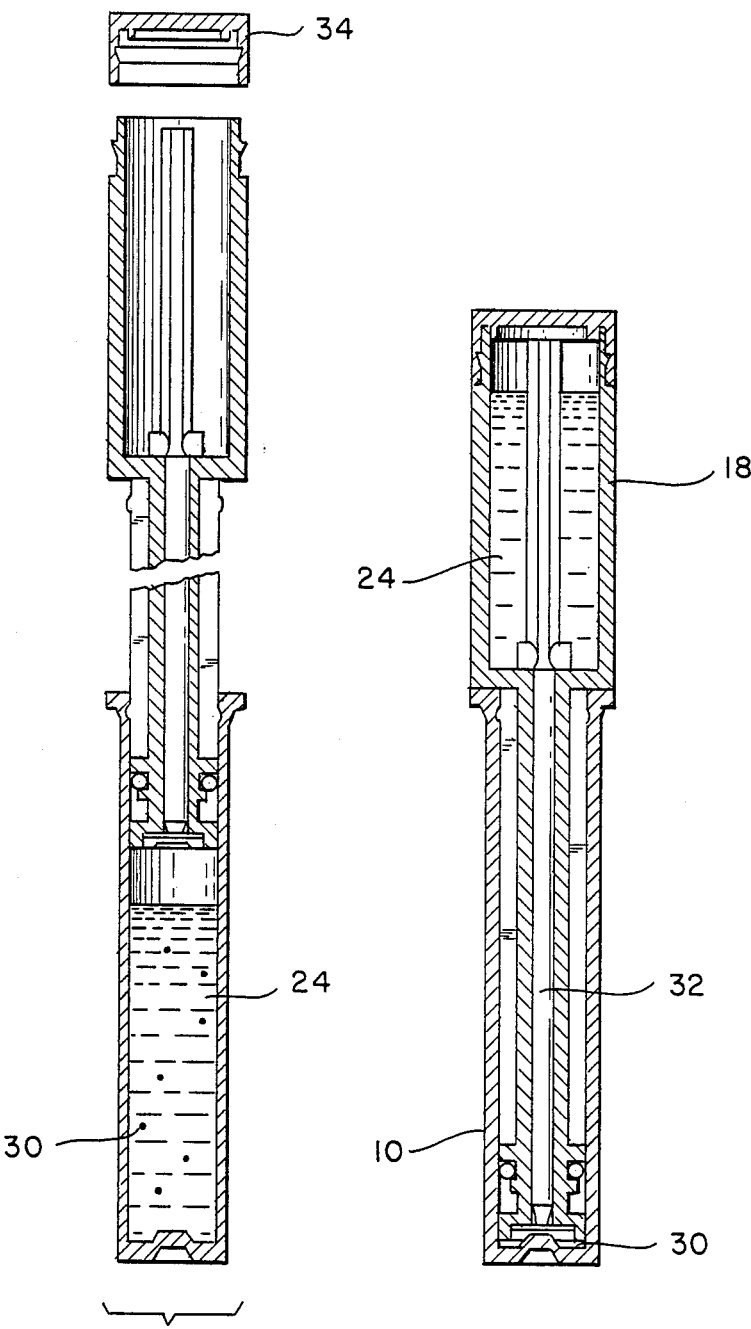
FIGS. 2A-B shows a LIDEX PS separator at the start (2a) and the end (2b) of the separation operation.

FIG. 2 is a schematical representation of the Lidex PS separator at the start (2a) and the end (2b) of the separation operation. The solid particles 30 initially suspended in the liquid phase 24 are fully separated and retained at the bottom of the mixing-reservoir 10. The additional feature of the system shown in FIG. 2 (and in FIG. 1d) is the plastic rod 32 placed in the axial channel 14 of the separator 12. The purpose of this rod is to displace its volume equivalent of the liquid phase up into the collecting container 18. The dimensions of the rod are such that there should be no interference with the free flow of the liquid phase in its passage through channel 14, while at the same time only an insignificant amount of liquid will remain in the channel 14 at the end of the separation. As a result, the radioactivity partitioned between the solid and liquid phases can be physically separated practically in toto. This, together with the hermetical sealing by the stopper 34 provides an important added flexibility to the assay protocol. With gamma-emitting tracers it is possible to count at choice both the solid phase and/or liquid phase simply by placing the separator in the well of the counter in the normal or upside-down position respectively.

The use of the rod is essential only in operations wherein a fully quantitative separation between solid and liquid phases is required, as for example in immunoassays.

As already mentioned in the preamble of the specification, the improved device according to the present invention can be successfully utilized as a very convenient equipment in the general field of physical separation of two or more phases either in liquid-liquid extraction, or liquid-solid extraction, in small scale or in large scale.

The shape of the elements of the new device can be varied as required for any specific use. The volume of the mixing-reservoir 20 and collecting container 18 can be varied as required by the volume of the liquid phase involved in the particular separation process. Element 18 can be a collecting container vessel of any desired geometrical shape and size. In general at a certain suitable height from the upper end of the mixer-separator 12, the collecting container 18 can be wider than the outer diameter of the mixing-reservoir 10.

According to one embodiment a ring is interposed between the upper end of the mixing-reservoir 10 and the element 18, which can be slided on the mixer-separator 12 and will thus determine the level of pushing in the mixer-separator 12 and accordingly the interface between the two phases, thus ensuring a complete removal of the upper phase from the mxing-reservoir 10. With the same principle, two or more rings could also be interposed for different positions of interface locations.

Figure 5:
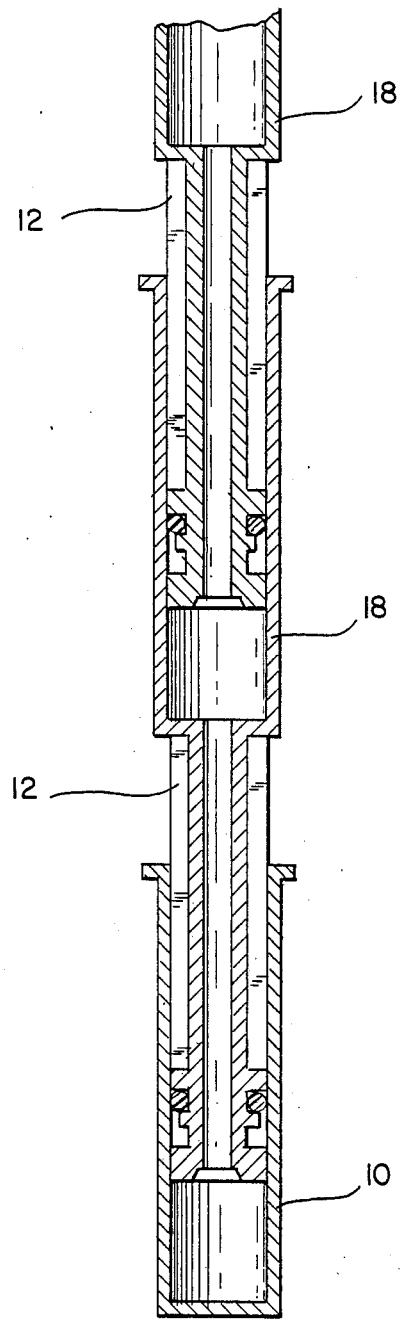
FIG. 5 illustrates a double separator.

The presence of the membrane is very important for the method according to the present invention. A general classification on the various types of membranes has already been mentioned above. The location of the membrane is always at the lowest part of the mixer-separator. In case of chromatographic analysis it may be encountered the case when two or more membranes are intercalated in the channel at different heights. In some particular cases, it is also possible to use a system consisting of two or more Lidex PS devices (FIG. 5) of the so called "cascade type" wherein two or more devices are superposed and will thus enable to obtain two or more fractions solid-free, or the fraction obtained from the first membrane being passed through another membrane, identical or different from the first one, thus producing through a cascade effect the desired degree of separation. Such a system may be very useful in water desalination by the process of reverse osmosis employing suitable membranes. A major operational feature of the Lidex PS method and device is based on the new dynamic principle of this invention whereby a moving membrane traverses the mixture to be separated. In conventional ultrafiltration and reverse osmosis systems the membrane is stationary, and only the liquid and/or particles are subject to movements. This allows for a more efficient mass transport and less danger of clogging the membrane. By an up and down movement at a defined rate of the mixer-separator, it is possible to use the downward movement for filtration and the upper movement for declogging the membrane.

An important function in the improved device, is the sealing element located at the base of the mixer-separator 12. The sealing element slides along the inner walls of the mixing-reservoir 10, at the same time staying in good contact with the inner walls permitting a snugly fitting of the mixer-separator 12 into the mixing-reservoir 10. Several variations may be encountered in the location and manufacture of the sealing element, without being outside the scope of the present invention. According to one embodiment, the sealing element consists of a rubber O-ring 28 having an orifice bore, adapted to slide along the inner walls of the mixing-reservoir. By pushing the mixer-separator 12, the upper layer liquid is aspirated through the orifice bore and the channel 14 being accumulated into the collecting container 18.

According to another embodiment, the rubber O-ring 28 is located slightly above the base of the mixer-separator, so that the rubber will not be in contact with the liquid lower phase from the mixing-reservoir 10. In this case no restriction on the type of rubber will be imposed.

Another advantage of the method according to the present invention with the novel device is the fact that it can be operated simultaneously on a series of devices which can be eminently amenable to automation without requiring complicated auxiliary equipment.

The operation with the device and even the analysis of the separated phase accumulated into the collecting container 18, can be carried out while the system is completely out of any manual handling. For instance after the liquid phase is separated and aspirated into the collecting container 18, the stopper 34 can be replaced by a vial (suitable to be adapted to the top of the container 18, FIG. 4) which might even contain the required reagents, and if desired including a suitable membrane which woould be permeable to the liquid from the collecting container 18. In this manner by replacing the stopper with the vial and turning down the entire device, the liquid from the collecting container 18 will pass (through the membrane if present) into the vial and react accordingly with the reagents therein. The vial with its content would be subsequently analysed by any known method.

Figure 6A:
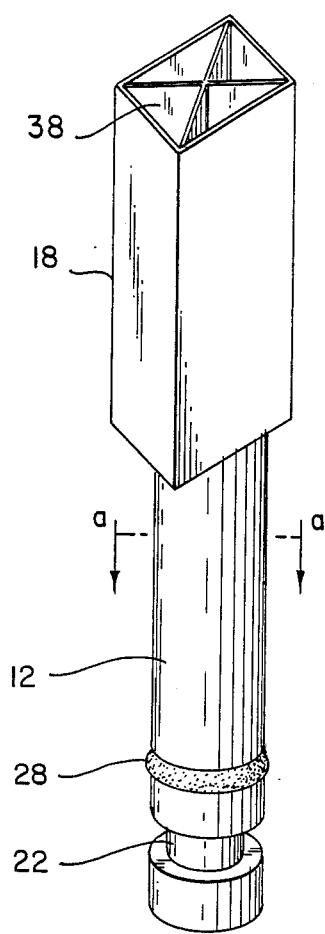
FIGS. 6A-B shows a mixer-separator.
Figure 6B:
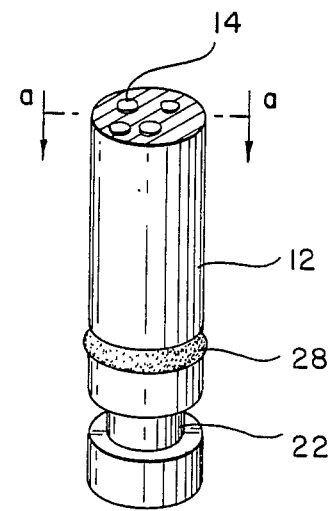

As already mentioned above it is also possible that the liquid absorbed through the mixer-separator will pass through two or more channels being conveyed to the collecting container 18 which in its turn can be divided into two or more compartments (see FIG. 6). In this manner it is possible to obtain several separate fractions and to carry out simultaneously two or more different analyses from the same liquid analyte in the device.

In another embodiment, the mixer-separator 12 is provided with means for increasing the volume of the air (or other gas) pocket to allow far greater versatility and flexibility in the choice of membrane for sterilization, ultrafiltration and reverse osmosis operations. The device shown in FIG. 7, illustrates a mixer-reservoir, FIG. 7a and a mixer-separator, FIG. 7b. The special feature, shown also in the enlarged detail of FIG. 7c, consists of an exit from the groove 12, through a tube 36, axially traversing the body of the mixer-separator 12, parallel to channel 14, through and out the collecting container 18; the upper part of the tube 36 can terminate into a gas container of desired volume so that the shock absorber, cushion effect described in this invention can be increased or decreased as desired and according to equation (vi) above. Another use of tube 36 would be for the introduction of a new portion of the mixture being separated into the mixing-reservoir 10, without having to dismantle the system. Connecting tube 36 to a vessel containing the separation mixture and moving the mixer-separator 12 in the upper direction would permit the introduction of an additional volume of the mixture into the mixer-reservoir 10.

The method of separation of the liquid phase according to the present invention will be hereinafter illustrated with a number of examples taken from immunoassay technique, wherein a clear separation is absolutely required, without being limited for this field only.

Although the invention will be described in the following examples in connection with certain preferred embodiments, it should be understood that it is not the intention to limit the invention to only these particular embodiments. On the contrary, it is intended to cover all the alternatives, modifications and equivalents, which may be included within the scope of the invention, as defined by the appended claims. Thus, the following examples, which include preferred embodiments, will serve to illustrate the practice of the invention. It should be understood that the particulars described below are examples only, for purposes of illustrative discussion, and are presented in order to provide what is believed to be the most useful and readily understood description of procedures, as well as of the principles and conceptual aspects of the invention.

EXAMPLE 1

Clinical sera digoxin radioimmunoassay ($^{125}$I) with Lidex Separators

Three parallel experiments designated A, B and C were carried out with ($^{125}$I) Digoxin Kit obtained from Bector Dickinson Immunodiagnostics (U.S.A.), Lot No. EN 7039. Experiment A was carried out according to the Kit directions. Experiment B was performed according to the Kit directions up to, and including the dextrancoated charcoal incubation step. At that point centrifugation was omitted and separation of the aqueous solution, containing the bound fraction, from the charcoal, containing the free fraction, was carried out by simply pushing in the mixer-separator of the Lidex PS separator into the mixing-reservoir A as far down as it would go. The Lidex assemblies were then taken directly to the gamma-counter.

In Experiment C the Lidex Separator was used with a liquid separating reagent (a mixture of t-amyl alcohol and methylisobutyl ketone) following the procedure described in Example 3 of the previous patent application No. 365.637-3.

A flow-sheet for the procedure and amounts of reagents used for the three parallel experiments is given in Table 1 below.

Included in each one of the three Experiments A, B and C were assays for 9 clinical serum samples supplied by the Toxicology Laboratory of Sheba Hospital, Tel-Hashomer, Israel. The same clinical serum samples were also assayed in the Tel-Hashomer Laboratory using a ($^{125}$I) Digoxin Kit supplied by Diagnostics Products, Catalogue No. KDIDI, according to the Kit instructions. Our analysis of the clinical serum samples were carried out as a "blind" experiment since the Tel-Hashomer assay values were disclosed to us only after completion of the three experiments A, B and C.

Each point of the standard curves and each clinical serum sample were assayed in duplicate. Radioactivity was determined by counting each tube for 30 seconds in a manual gamma-counting instrument Elscint INS-IIE. The results for the standard curves in the three experiments expressed as % Bound/Bound zero are summarized in Table 2.

The values for Digoxin found in the clinical serum samples, expressed in nanogram per ml, as determined from the respective standard calibration curves, are given in Table 3 in columns A, B and C corresponding to the three experiments A, B and C. The last column in Table 3 reports the respective Digoxin values obtained at the Tel-Hashomer Laboratory for the same clinical serum samples. The excellent fit of these results provides conclusive proof of the major advantages and superiority of our new methods and device for a variety of mass transfer operations.

TABLE 1

Flow sheet for three parallel radioimmunoassays comparing Lidex Separation Systems with a commercial Kit separation method.

| Operation | Experiment A Becton Dickinson Assay Directions | Experiment B Lidex PS separation | Experiment C Lidex Liquid Separating Reagent |
|---|---|---|---|
| Add standard or serum sample | 50 μl | 50 μl | 50 μl |
| Add [$^{125}$I] Digoxin tracer | 1000 μl | 1000 μl | 700 μl |
| Add Digoxin antiserum | 100 μl | 100 μl | 100 μl |
| Incubate at room temp. for | 30 min. | 30 min. | 30 min. |
| Add charcoal reagent | 0.5 ml | 0.5 ml | — |
| Add Lidex Separating Reagent and insert Lidex Piston | — | — | 1.5 ml |
| Vortex for | 1-2 sec. | 1-2 sec. | 15-20 sec. |
| Incubate at room temp. for | 2-5 min. | 2-5 min. | — |
| Allow to stand at room temp. for | — | — | 5-10 min. |
| Centrifuge at 1000xg or greater for | 10-20 min. | No centrifugation required | No centrifugation required |
|  |  | Push Lidex Piston into assay tube as far as it will go and cap. | |
| Counting | After centrifugation transfer supernatants in new numbered test tubes and count the radioactivity of the supernatants | No transfer required. Count directly the upper liquid phase in the Lidex Assembly | No transfer required. Count directly the lower aqueous phase in the Lidex assembly. |

TABLE 2

Digoxin ($^{125}$I)RIA Standard Calibration Curves for three parallel assays A, B and C.

| | % B/Bo (duplicate values) | | |
|---|---|---|---|
| Digoxin Standard (ng/ml) | Experiment A Becton Dickinson Assay Directions | Experiment B LIDEX PS Separator | Experiment C LIDEX-Liquid Separating Reagent |
| 0.5 | 87 | — | 79 |
|  | 93 | 76 | 80 |
| 1.0 | 78 | 69 | 68 |
|  | 81 | 65 | 68 |
| 1.5 | 74 | 60 | 61 |
|  | 72 | 57 | 59 |
| 2.0 | 62 | 47 | 52 |
|  | 64 | 47 | 49 |
| 3.0 | 47 | 38 | 40 |
|  | 50 | 38 | 42 |
| 5.0 | 34 | 26 | 32 |
|  | 32 | 24 | 33 |

TABLE 3

Digoxin values of clinical serum samples determined in three parallel assays A, B and C and (independently) at Sheba Hospital Laboratory - Tel Hashomer.

| | Digoxin concentration (ng/ml) | | | |
|---|---|---|---|---|
| Serum No. | Assay A Becton-Dickinson Assay Directions | Assay B LIDEX PS Separator | Assay C LIDEX Liquid Separating Reagent | Tel-Hashomer Diagnostic Products Assay Directions |
| 1 | <0.5 | 0.3 | 0.5 | 0.4 |
| 2 | 1.8 | 2.3 | 1.9 | 2.2 |
| 3 | 0.7 | 0.9 | 0.9 | 1.0 |
| 4 | <0.5 | 0.7 | 0.6 | 0.6 |
| 5 | 1.4 | 1.5 | 1.6 | 1.6 |
| 6. | 1.0 | 1.4 | 1.4 | 1.3 |
| 7 | <0.5 | 0.7 | 0.7 | 0.5 |
| 8 | 0.7 | 1.1 | 1.2 | 1.4 |
| 9 | 4.1 | 4.1 | 3.4 | 5.7 |

EXAMPLE 2

DIGOXIN-RIA-(3H) WITH LIDEX SEPARATORS

Materials and Methods ($^3$H) Digoxin Kit obtained from Becton-Dickinsom Immunodiagnostics, New York (U.S.A.) Lot No. EG. 0488 Lidex Separators (fitted with a glass fibers membrane) produced at the Technion (Haifa, Israel). Liquid extracting agent was prepared from t-amyl-alcohol with 50% t-butyl-methyl ether and was saturated with Phosphate-Saline buffer (Becton-Dickinson, Cat. No. 213519).

A procedure was performed according to the kit directions for use as will be summarized in the following Table.

Radioactivity was determined using Liquid Scintillation counter suitable for measuring ($^3$H). (Beta-counter instrument, Packard). Each sample was counted for 2 minutes.

TABLE 4

Flow-sheet for two parallel Radioimmunoassays comparing the Lidex Separation Systems, with a commercial Kit.

|  | A<br>Becton-<br>Dickinson<br>Assay-<br>System | B<br>Lidex PS<br>Separation |
|---|---|---|
| Digoxin Standard | 200 μl | 200 μl |
| ($^3$H) Digoxin Tracer | 100 μl | 100 μl |
| Digoxin Anti-serum | 100 μl | 100 μl |
| Phosphate-Saline Buffer | 600 μl | 300 μl |
| Incubation | 30 min. (R.T.) | 30 min. (R.T.) |
| D.C.C. | 500 μl | |
| Lidex Separating Reagent | | 1500 μl |
| Vortex | 1-2 sec. | 20 sec. |
| Incubation | 10 min. (R.T.) | |
| Allow to stand for | | 2 min. (R.T.) |
| Centrifugation | 1000xg for 10-20 min. | not required. |
| Counting | Decantation of supernatants into 10 ml Insta-Gel and count radioactivity | Insert Lidex PS separator and decant upper phase into 10 ml Insta-Gel and count radioactivity |

The following Table summarizes the results obtained using the two methods (A, B):

TABLE 5

| Standard Digoxin (ng/ml) | A Percent (%) B/Bo | B Percent (%) B/Bo |
|---|---|---|
| 0.5 | 88 | 85 |
| 1.0 | 78 | 70 |
| 1.5 | 60 | 51 |
| 2.0 | 52 | 40 |
| 3.0 | 44 | 34 |
| 5.0 | 27 | 24 |

The calculated values obtained from regression line curves of cpm vs log conc. for the two methods had a correlation coefficient of 0.9378.

EXAMPLE 3

PROLACTIN KIT (BIODATA-CODE 1803 $^{125}$I RIA WITH DOUBLE ANTIBODY TECHNIQUE

Two parallel experiments were carried out. Experiment A was performed exactly according to the kit instructions while Experiment B was carried out according to the kit instructions up to but not including the centrifugation step. Instead of centrifugation the separation of the free and bound phase was carried out with the Lidex separator fitted with a glass-fibre membrane as described in Example 1 for the Digoxin RIA Kit. The experimental results calculated as B/Bo and the clinical values obtained from the standard curves are shown in the following Tables.

These experiments were carried out with the kit reagents without any prior work to optimize the assay conditions for application of the Lidex separation technology. In order to demonstrate the versatility of the Lidex PS separator each test tube in Experiment B was counted twice to determine both the bound fraction and (turning device upside down) the free fraction. The results are represented as B/Bo where the actual bound was calculated using the appropriate corrections.

| HPRL - CLINICAL VALUES (ng/ml) | | | |
|---|---|---|---|
| | | LIDEX | |
| SERUM CODE | TRADITIONAL Bound Corrected | Bound Corrected | Free Corrected |
| M 9 | 11.68 | 13.96 | 12.18 |
| M 7 | 10.00 | 9.67 | 9.94 |
| L | 4.07 | 5.08 | 5.74 |
| H | 76.42 | 100.77 | >100* |
| H (1:2) | 75.64 | 79.80 | 83.06 |
| ♂ | 2.40 | 2.65 | 3.70 |
| ♂ | 5.28 | 6.18 | 7.39 |
| ♀ | 4.02 | 4.43 | 6.26 |
| ♀ | 9.94 | 10.73 | 13.06 |
| Menop. ♀ | 7.31 | 7.71 | 8.69 |
| menop. ♀ | 4.70 | 6.78 | 6.89 |
| THR-stim. —15' | 76.18 | 83.17 | 49.94 |
| 0' | 87.81 | >100* | >100* |
| +15' | 86.53 | >100* | >100* |
| +30' | >100* | >100* | >100* |
| +60' | 94.68 | >100* | >100* |
| +120' | 89.93 | >100* | >100* |
| Ortho-Ligand | | | |
| 10T10 2A | 1.89 | 1.90 | 2.35 |
| 10T10 2B | 1.58 | 1.53 | 3.14 |
| 10T10 2C | 1.84 | 2.76 | 2.12 |

*out of the standard curve

| HPRL - KIT EVALUATION BY TWO DIFFERENT SEPARATION METHODS | | | |
|---|---|---|---|
| A - traditional separation method by centrifugation. | | | |
| B - LIDEX - system (fitted with a glass fiber membrane) | | | |
| HPRL - STANDARD CURVES | | | |
| Standard | | LIDEX | |
| concentration (ng/ml) | Traditional B/Bo | Bound corrected (B/Bo) | Free corrected (B/Bo) |
| 2.0 | 0.85 | 0.89 | 0.94 |
| 5.0 | 0.73 | 0.73 | 0.77 |
| 10.0 | 0.56 | 0.56 | 0.52 |
| 20.0 | 0.38 | 0.34 | 0.35 |
| 40.0 | 0.23 | 0.23 | 0.20 |
| 100.0 | 0.15 | 0.13 | 0.09 |
| Standard Assay system - curve parameters. | TRADITIONAL Bound corrected | LIDEX Bound corrected | Free corrected |
| Maximum binding (%) | 38.20 | 38.80 | 34.60 |
| Midrange curve (ng/ml) | 12.76 | 12.40 | 12.25 |
| Sensitivity (ng/ml) | 0.79 | 1.76 | 3.14 |

EXAMPLE 4

PSH KIT (FOLICAL STIMULATING HORMONE, BIODATA-CODE 1103 $^{125}$I RIA KIT WITH DOUBLE ANTIBODY

The assay was performed as described in Example 3 and the results were also calculated as in the same experiment (Example 3).

The following Tables show the results obtained:

| FSH - DAB KIT EVALUATION BY TWO DIFFERENT SEPARATION METHODS | | | |
|---|---|---|---|
| Traditional separation method by centrifugation LIDEX - system | | | |
| Standard Assay system | TRADITIONAL | LIDEX | |
| Curve parameters | Bound corrected | Bound corrected | Free corrected |
| Maximun binding (%) | 41.60 | 38.30 | 38.50 |
| Midrange curve (MIU/ml) | 8.11 | 8.10 | 2.40 |
| Sensitivity (mIU/ml) | 0.35 | 0.94 | 0.17 |
| FSH - Standard Curve | | | |
| | | LIDEX | |
| Standards concentration (ng/ml) | TRADITIONAL (B/Bo) | Bound corrected (B/Bo) | Free corrected (B/Bo) |
| 2.0 | 0.78 | 0.80 | 0.53 |
| 5.0 | 0.62 | 0.64 | 0.35 |
| 10.0 | 0.42 | 0.40 | 0.26 |
| 20.0 | 0.32 | 0.33 | 0.19 |
| 40.0 | 0.19 | 0.18 | 0.15 |
| 100.0 | 0.09 | 0.06 | 0.05 |

EXAMPLE 5

TOTAL THYROXIN (T$_4$)

Total Thyroxin (T$_4$) was determined by an RIA kit with a $^{125}$I T$_4$ tracer and a young's T$_4$ antibody.

The performance of the experiment was the same as described for Example 2 using Biodata kit components.

A standard curve and clinical sera were assayed in both systems.

A Lidex PS separator fitted with two different glass fibers discs (membranes in series) was utilized.

The following Table summarizes the results obtained for both separatin methods.

| T4 - KIT EVALUATION BY TWO DIFFERENT SEPARATION METHODS | | |
|---|---|---|
| Traditional separation method by centrifugation | | |
| LIDEX PS - system fitted with two membranes | | |
| T$_4$ - STANDARD CURVE | | |
| Standard Method concentration (μg %) | Traditional Bound Corrected (B/Bo) | Lidex fitted with 2 membranes Bound Corrected (B/Bo) |
| 1.5 | 0.83 | 0.85 |
| 3.0 | 0.69 | 0.74 |
| 6.0 | 0.53 | 0.67 |
| 12.0 | 0.39 | 0.56 |
| 24.0 | 0.26 | 0.44 |
| T$_4$ - CLINICAL VALUES (μg %) | | |
| SERUM CODE | TRADITIONAL | LIDEX |
| M 9 | 6.76 | 6.62 |
| L | 1.70 | 1.30 |
| H | 22.44 | 31.00* |
| Plasma -5 | 9.66 | 9.80 |
| Plasma -18 | 16.84 | 17.80 |
| Plasma -6 | 9.76 | 10.58 |
| Plasma -30 | 5.05 | 4.53 |
| Plasma -29 | 7.00 | 7.75 |
| Ortho-Ligand | | |
| 10T10 2A | 0.81 | 0.67 |
| 10T10 2B | 7.24 | 6.74 |
| 10T10 2C | 13.61 | 15.25 |
| Sensitivity | 0.31 μg % | 0.42 μg % |

*out of the standard curve

EXAMPLE 6

FERRITIN $^{125}$I RIA KIT (BIODATA) WITH A DOUBLE ANTIBODY AND POLYETHYLENE GLYCOL (P.E.G.) AS A PRECIPITANT

The following kit was also performed as described in the previous examples (2, 3 and 4) using the Lidex PS system.

The following tables show results obtained for standard curve and clinical serum samples.

Ferritin - Double-Antibody - P.E.G. kit evaluation by two different separation methods.
Traditional separation method by centrifugation and -continued Lidex PS - system fitted with two different glass fibers membranes.

A - STANDARD CURVE

| | Traditional | Lidex PS with 2 membranes | |
|---|---|---|---|
| Standard Method concentration (ng/nl) | Bound Corrected (B/Bo) | Bound corrected (B/Bo) | Free corrected (B/Bo) |
| 20.0 | 0.92 | 0.89 | 0.89 |
| 50.0 | 0.76 | 0.72 | 0.74 |
| 150.0 | 0.47 | 0.44 | 0.45 |
| 400.0 | 0.27 | 0.24 | 0.24 |
| 1000.0 | 0.14 | 0.12 | 0.11 |

B - CLINICAL VALUES (ng/nl).

| | | Lidex with 2 membranes | |
|---|---|---|---|
| Serum No. | Traditional | Bound corrected | Free corrected |
| 1 | 10.9 | 13.4 | 10.6 |
| 2 | <20 | <20 | <20 |
| 3 | 71.4 | 73.6 | 70.3 |
| 4 | 32.1 | 36.7 | 36.3 |
| 5 | 135.7 | 114 | 132 |
| 6 | 56.7 | 53.8 | 68.4 |
| 7 | <20 | <20 | <20 |
| 8 | <20 | <20 | <20 |

EXAMPLE 7

Use of Lidex Separator in Reverse Osmosis Operation

This example illustrates the feasibility of reverse osmosis (R.O.) operation using commercially available membranes fitted into a Lidex PS.

Materials and Methods

An aromatic polyamide membrane (produced by Ramot Plastics—Tel-Aviv, Israel) was cut and inserted into the lower part of a mixer-separator B of a Lidex PS.

Tap water was placed into a mixing-reservoir and the water from the mixing-reservoir was passed through the R.O. membrane by gliding the mixer-separator into the mixing-reservoir.

Flow rate of 10 ml/h was obtained.

Results

The conductivity of water before and after this operation was determined. It was found that more than 40% salt rejection resulted. (Tap water conductivity was 600 $\mu$mho before the Lidex PS operation and the conductivity was reduced to 350 $\mu$mho after the operation).

By using a slower flow rate with the same membrane in the Lidex PS separator it was possible to achieve up to 95% salt rejection.

EXAMPLE 8

Sterilization of E. coli Suspension

Materials

1. Trypton Medium (Difco-registered Trade Mark-)—Trypton Medium for cultivation of bacteria was prepared as recommended by Difco. 10 grs. of trypton +5 grs. of sodium chloride were dissolved in 1 liter distilled water. 6×125 ml. Erlenmeyer with side arm were filled with 20 ml of trypton medium and plugged with cotton corks.

2. Lidex separation technique—Regular Lidex PS separators were used. Three filers were put in each separator: 1 layer of millipore ®—Teflon TM filter 0.45$\mu$ and on both sides filters GF/A provided by Whatman (Glass Microfibre Filter).

3. Suspension of E. coli in saline was used as innoculum.

4. Erlenmeyers containing the trypton medium and Lidex separators (already with the filters) were autoclaved for 30 minutes in 120° C. and 1.2 kg/cm².

5. Sterile conditions were kept through the whole experiment.

6. Klett Summerson photometric colorimeter with green filter was used to follow bacteria growth by measuring light scattering expressed as Klett Units.

PROCEDURE

1. Filtration Experiment—Suspension of E. coli in saline was filtered, using Lidex separators with A-Teflon TM -A filters. Optical density of the solution was measured before and after the filtration.

2. Control Experiment—1.5 ml of E. coli suspension were transferred to 125 ml Erlenmeyers with side arm which contained 20 ml of trypton medium. This experiment was performed with 3 replicates.

3. Lidex Experiment—1.5 ml of E. coli Suspension were transferred to a Lidex device and filtered through Lidex separator with A-Teflon TM -A filters. Hand pressure was used to press the separator. The filtrate was transferred to a 125 ml Erlenmeyer with side arm, which contained 20 ml of trypton medium. This experiment was done with 4 replicates.

4. The 7 Erlenmeyers were incubated in 37° water bath with constant shaking. Bacteria growth was followed by measuring light scattering (with Klett photometer) every 1 hour.

Results

| Experiment 1. Klett Units | | Experiments II–IV expressed in Klett Units | | | | | |
|---|---|---|---|---|---|---|---|
| | | Time | 0 | 2 h | 3 h | 4 h | 5 h | 5[1] |
| E. Coli Suspension | 25 | Control I | 14 | 20 | 25 | 34 | 60 | 71 |

| Experiment 1. | Results Experiments II–IV expressed in Klett Units | | | | | | |
|---|---|---|---|---|---|---|---|
| Klett Units | Time | 0 | 2 h | 3 h | 4 h | 5 h | 5¹ |
| E. Coli Suspension | Control II | 13 | 17 | 21 | 34 | 57 | 70 |
| after filtration | Control III | 14 | 18 | 23 | 34 | 58 | 68 |
| with Lidex | Lidex I | 4 | 5 | 6 | 6 | 8 | 6 |
| Separators | Lidex II | 4 | 6 | 6 | 5 | 8 | 7 |
|  | Lidex III | 4 | 5 | 7 | 6 | 8 | 10 |
|  | Lidex IV | 4 | 4 | 5 | 4 | 8 | 11 |

(E. Coli Suspension value: 0)

EXAMPLE 9

Sterilization of E. coli Suspension

Materials:

Lidex Separator—(as described in FIG. 7) Mixing-reservoir A and mixer-separator B equipped with millipore ®-Teflon TM 0.45μ filter between 2 sinter glass layers.

Trypton Medium (Difco)—(registered Trade Mark)—prepared as recommended by Difco. 10 grs. of Trypton + 5 grs. of Sodium Chloride were dissolvd in 1 liter distilled water. 20 ml of the trypton medium were transferred to a 125 ml Erlenmeyer.

Sterilization: The mixer-separator B with the filters and the Erlenmeyer containing the trypton medium were autoclaved 30 minutes in 120° C.

Procedure 1. 250 ml of E. coli Suspension (in distilled water) were filtered through millipore ®-Teflon 0.45μ filter using Lidex separator. Optical densities (O.D.) of the E. coli Suspension and the filtrate were measured using Giford-4009 spectrophotometer.

2. 1 ml of the filtrate was transferred into an Erlenmeyer with 20 ml trypton medium and incubated 4 hours at 37° with constant shaking.

| Results: | |
|---|---|
|  | OD$_{540}$ |
| Water | 0.004 |
| E. Coli Suspension | 0.227 |
| Filtrate | 0.005 |

No bacteria growth was observed after 4 hours.

EXAMPLE 10

Use of Protein A-Sepharose CL-4B in RIA

This example illustrates the use of a mobile bed as a selective barrier instead of a filter membrane. We have chosen a sepharose TM support but any other suitable material could be used such as ion exchange resins, etc.

Prolactin RIA assay was performed to check the possibility of using Protein A—Sepharose CL-4B for binding the Anitgen-Antibody complex instead of Double Antibody. Lidex PS Separator were used instead of centrifugation.

Procedure 60 mg of Protein A—Sepharose CL-4B were filled into channel of the mixer-separator in which the lower part was fitted with a glass fibre filter and the upper part was fitted with a piece of cotton wool. Prolactin RIA Kit was obtained from Hypolab (Switzerland). Protein A—Sepharose CL-4B was obtained from Pharmacia (Sweden).

Hypolab Double Antibody Method

Procedure as recommended by Hypolab. 4 replicates of NSB (non-specific binding) and 4 replicates of Bo were tested:

I. NSB tube—0.2 ml buffer were mixed with $^{125}$I-hPRL (prolactin) and incubated overnight at room temperature.

II. Bo tubes—0.1 ml buffer were mixed with 0.1 ml $^{125}$I-hPRL and 0.1 ml Anti-hPRL serum and incubated overnight at room temperature.

III. Following overnight incubation, 0.1 ml Anti RGG (Rabbit gamma globulin) was added to all tubes and after 2 hours of incubation 2 ml bidistilled water were added to all tubes. Tubes were centrifuged for 30 minutes at 2000×g in the cold.

IV. Supernatants were decanted and pellets were counted using LKB Gamma Counter.

Lidex—8% Peg/Double Antibody Method

Steps I and II as in Hypolab method.

III. 1½ ml of 8% Peg/Dab (Polyethylene glycol/double antibody) were added to each tube.

IV. Lidex separators were used. Separation time 2'40".

Lidex—Protein A—Sepharose CL-4B Method

Steps I and II as in Hypolab.

III. 1½ ml RIA buffer were added to each tube.

IV. Lidex separation technique was used. Lidex separators with filter A were filled with 60 mg of Protein A—Sepharose CL-4B. Separation time 5'14".

| | Results | | | | | |
|---|---|---|---|---|---|---|
| | Hypolab - Dab/Water | | Lidex - 8% Peg/Dab | | Lidex - Protein A | |
| | cpm | mean cpm | cpm | mean cpm | cpm | mean cpm |
| total | 13685 | 13751 | 13883 | 13822 | 13861 | 13835 |
| total | 13817 | | 13761 | | 13810 | |
| NSB | 620 | 665 | 1013 | 1213 | 2126 | 1920 |
| NSB | 687 | | 1118 | | 1665 | |
| NSB | 846 | | 1399 | | 1905 | |
| NSB | 507 | | 1323 | | 1986 | |
| Bo | 6112 | 6225 | 6687 | 6638 | 6454 | 6192 |
| Bo | 6205 | | 6546 | | 5780 | |

-continued

| | Results | | | | |
|---|---|---|---|---|---|
| | Hypolab - Dab/Water | | Lidex - 8% Peg/Dab | | Lidex - Protein A |
| | cpm | mean cpm | cpm | mean cpm | cpm | mean cpm |
| Bo | 6359 | | 6670 | | 6342 | |
| Bo | — | | 6649 | | — | |
| *maximum binding | | 40.4% | | 39.2% | | 30.9% |

∘ $\frac{Bo\ (cpm) - NSB\ (cpm)}{total\ (cpm)} \times 100$

We claim:

1. A method for carrying out mass transport and substantially quantitative physical separation of one or more components from one phase to another phase without the need for centrifugation, the phases being both liquid, or liquid-solid or liquid-gas-solid, or liquid-gas-liquid, said mass transport and physical separation operations being substantially quantitative and carried out in the same device, which comprises the steps of introducing the phases to be contacted including a liquid phase into a vertical mixing reservoir having an inner wall, mixing the components, pushing into said mixing reservoir with a sliding movement a mixer-separator possessing at least one barrier and a sealing element located above said at least one barrier so as to force a clear liquid phase through said at least one barrier and convey it through at least one channel in the mixer-separator into a container at the upper end of the mixer-separator, and accumulating a gas cushion between said sealing element and the surface of the liquid phase in said mixing reservoir sufficient to decrease the pressure exerted on said at least one barrier in response to the sliding movement of said mixer-separator into said mixing reservoir and to force back into said mixing reservoir any of the liquid which has crept up along the inner wall of the mixing reservoir above the lower end of the mixer-separator, said gas cushion being maintained during the entire sliding movement of the mixer-separator into the mixing reservoir until all of the liquid phase is forced through said at least one barrier, whereby substantially quantitative separation of the liquid phase can be accomplished.

2. A method according to claim 1, wherein said at least one; barrier is porous, the pores being smaller than the solid particles present in the phases to be separated.

3. A method according to claim 1, wherein said at least one barrier is made from a chemically reactive material which reacts with a constituent of the phases to be contacted that permeates it.

4. A method for carrying out mass transport and subsequent physical, substantially quantitative separation of one or more components from one phase to another phase, the phases comprising a solid and a liquid phase and including in each instance an upper liquid phase, in the same device, which comprises:

a vertical mixing reservoir, having an inner diameter, an outer diameter, an inner wall an an upper end;

a mixer-separator snugly fitted into said reservoir for sliding movement therein and including means defining at least one channel passing axially through said mixer-separator, said mixer-separator including at its lower end at least one barrier which is selectively permeable to the upper liquid phase in said mixing reservoir and at its upper end a container which has a top and into which opens said at least one channel for accumulating separated liquid from said upper liquid phase from the mixing-reservoir forced through said barrier and said at least one channel in response to sliding movement of said mixer-separator is pushed down into said mixing reservoir;

a sealing element surrounding said mixer-separator at a preselected distance above the lower end of said mixer-separator, said sealing element being positioned above said barrier; and means defining a space positioned in the axial direction between said barrier and said element, for providing a gas cushion for decreasing the pressure exerted on said barrier in response to sliding movement of said mixer-separator into said mixing reservoir, the configuration of said space and the gas cushion being selected so as to force back into said mixing reservoir any of the liquid phase which has crept up along the inner wall of the mixing reservoir above the lower end of the mixer-separator, whereby substantially quantitative separation of the upper liquid phase can be accomplished, said method comprising the steps of:

introducing the phases to be contacted including a liquid phase into said vertical mixing reservoir, mixing the components, pushing into said mixing reservoir with a sliding movement said mixer-separator possessing at least one barrier and said sealing element located above said at least one barrier so as to force a clear liquid phase through said at least one barrier and convey it through said at least one channel in the mixer-separator into a container at the upper end of the mixer-separator, and accumulating a gas cushion between said sealing element and the surface of the liquid phase in said mixing reservoir sufficient to decrease the pressure exerted on said at least one barrier in response to the sliding movement of said mixer-separator into said mixing reservoir and to force back into said mixing reservoir any of the liquid phase which has crept up along the inner wall of the mixing reservoir above the lower end of the mixer-separator, said gas cushion being maintained during the entire sliding movement of the mixer-separator into the mixing reservoir until all of the liquid phase is forced through said at least one barrier, whereby substantially quantitative separation of the liquid phase can be accomplished.

5. A method according to claim 4, wherein the configuration and size of said means defining said space and the gas cushion are selected so as to provide that the pressure $P_M$ exerted on the at least one barrier located in a membrane cavity is determined in accordance with the equation:

$$P_2 = \alpha P_M + \beta \ln P_M - \delta$$

wherein $P_M > 1$ and $\alpha$, $\beta$ and $\delta$ are positive parameters:

$$\alpha = 1 + \frac{k}{V_1 - V_2}$$

$$\beta = +\frac{P_1 V_b}{V_1 - V_2} \text{ and}$$

$$\delta = [P_1 V_b \ln P_1 + k(P_1 + \pi)]/V_1 - V_2$$

and wherein $P_2$ is the pressure exerted on the mixer separator, $V_1$ is the volume in the mixing-reservoir below the membrane cavity, $V_2$ is the volume in the mixing reservoir, $P_1$ is the atmospheric pressure, $V_b$ is the volume of the air cushion, $\pi$ is the osmotic pressure and k is a membrane constant.

6. A method according to claim 4, wherein said device further comprises a stopper positioned at the top of said container, and means associated with said stopper and container for effecting closure of said stopper in response to completion of sliding movement of said mixer-separator into said mixing reservoir, and said method further comprises the step of effecting closure of said stopper upon completion of said sliding movement.

7. A method according to claim 4, further comprising the step of inserting a rod into said at least one channel of the mixer-separator and displacing substantially the entire volume of the liquid phase from said at least one channel into the container.

8. A method according to claim 7, wherein said at least one channel and said rod have a length which is sufficient to enable a physical separation of a first separated phase located in said container and a second unseparated phase left in said mixing reservoir which permits independent counting of radioactivity in said respective first and second phases.

9. A method according to claim 4, wherein said step of accumulating a gas cushion includes introducing pressure through at least one channel tube passing through said mixer-separator and connecting said space to an external source.

10. A method according to claim 4, wherein said at least one barrier comprises an adsorptive barrier, a diffusive barrier, an ion-exchange barrier, an osmotic barrier, an ultrafiltration barrier or a nonselective barrier having an inert behavior.

11. A method according to claim 4, wherein said at least one barrier comprises a bed in the form of a compact disc.

12. A method according to claim 4, wherein said at least one barrier comprises a membrane.

13. A method according to claim 4, wherein said at least one barrier comprises a cartridge containing an ion-exchange resin.

14. A method according to claim 4, wherein said at least one barrier comprises an osmotic or ultrafiltration membrane.

15. A method according to claim 4, wherein said means defining a space includes a portion of said mixer-separator located at the lower end of the mixer-separator and having a diameter substantially equal to the inner diameter of said mixing reservoir, said portion being separated axially from said sealing element and defining between itself and said sealing element a gap of generally annular configuration in said mixer-separator.

* * * * *